United States Patent [19]

Lipko et al.

[11] 4,436,520

[45] Mar. 13, 1984

[54] LOW GLOSS FILMS OF ENHANCED ADHESION

[75] Inventors: Robert J. Lipko, Llewellyn; Douglas J. Laurent, Auburn, both of Pa.

[73] Assignee: Exxon Research & Engineering Co., Florham Park, N.J.

[21] Appl. No.: 332,367

[22] Filed: Dec. 21, 1981

[51] Int. Cl.[3] .............................................. A61F 13/02

[52] U.S. Cl. .................................... 604/385; 604/389; 604/378; 428/523; 428/332; 428/156; 428/172

[58] Field of Search ................ 156/219; 428/500, 332; 604/381, 378, 385, 389

[56] References Cited

U.S. PATENT DOCUMENTS

| | | | |
|---|---|---|---|
| 3,559,648 | 2/1971 | Mason | 604/389 |
| 4,214,028 | 7/1980 | Shortway et al. | 156/219 |
| 4,273,819 | 6/1981 | Schmidle et al. | 156/219 |

*Primary Examiner*—George F. Lesmes
*Assistant Examiner*—E. Rollins Buffalow
*Attorney, Agent, or Firm*—Roland A. Dexter; Robert L. Graham

[57] ABSTRACT

The adhesion property of a surface of a polyolefin film, for example a polyethylene film, having a gloss of less than about 8 is enhanced with the mean value of the maximum profile height less than 150 and with mean maximum peak to valley height less than 230.

3 Claims, No Drawings

LOW GLOSS FILMS OF ENHANCED ADHESION

This invention relates to non-shiny polyolefin films. More particularly, it relates to matte finish polyethylene films of improved surface adhesion.

BACKGROUND OF THE INVENTION

Polyolefin films have many applications which require that the reflective or shiny nature of the film be reduced in gloss. One such application is the back sheet of a diaper which is conventionally constructed of an absorbent inner layer disposed between a non-woven top sheet and film back sheet having closure tabs to secure the diaper in place. The exposed surface of the film functioning as the diaper back sheet is produced by embossing the surface of the film to reduce the gloss to an acceptable level.

Unfortunately the embossing materially reduces the adhesion of the embossed surface for the closure tabs so that the diaper is no longer secure in its use on the infant.

Embossing of the surface of polyolefin films to reduce the gloss of films used in packaging of goods, e.g. rolls of toilet tissue, to be purveyed in the supermarket is quite common. Unfortunately the embossing provides an irregular surface toward printing inks and other indicia imposed on the surface making the graphics unacceptable.

It is an object to this invention to develop a polyolefin film of relatively low gloss having a surface of improved adhesion.

SUMMARY OF THE INVENTION

It has been discovered that in embossed films of polyethylene having a gloss of no greater than 8, the adhesion of the embossed surface is markedly enhanced when said surface has a mean value of maximum profile height of less than 150 and maximum peak to valley height of less than 230.

In accordance with this invention there is provided a polyolefin film having at least one surface exhibiting the properties of a 45° gloss of no greater than 8, a mean value of maximum profile height ($R_{pm}$) of less than 150, preferably less than 100, optimally less than about 80, and a mean maximum peak to valley height ($R_{tm}$) of less than 230, preferably less than 200, optimally 160, whereby said surface has enhanced adhesion.

In accordance with this invention there is also now provided a disposable diaper having a diaper back sheet, non-woven top sheet, absorbent inner layer and closure tabs, wherein the exposed surface of said diaper back sheet has a 45° gloss of no greater than 8, a mean value of maximum profile height ($R_{pm}$) of less than 150, and a mean maximum peak to valley height ($R_{tm}$) of less than 230 whereby said surface has enhanced adhesion.

It has also been found that indicia can be more legibly produced through such means as printing onto the low gloss film of the invention.

DETAILED DESCRIPTION OF THE INVENTION

The polyolefin films from which embodiments of the invention can be realized include ethylene homopolymers or copolymers with other unsaturated monomers. Preferred unsaturated monomers for copolymerization with ethylene comprise acrylic acid, esters of acrylic acid, vinyl acetates or other vinyl esters, and olefinic monomers having from 3 to about 8 carbon atoms. The ethylene content of the copolymer, i.e. that portion attributible to ethylene monomer, will comprise at least about 80% by weight of the copolymer. Preferably, the ethylene content of the copolymer will comprise 90 to 95% by weight. Also preferred are propylene homopolymers and copolymers.

The methods employed to form the polymers useful herein are not critical to the success of this invention and will be well known to those skilled in the art. In general, with respect to ethylene homopolymers and copolymers of ethylene with acrylic acid and acrylic or vinyl esters, it has been found preferable to use conventional high pressure and high temperature techiques to carry out the polymerization. The polymeric films or sheets formed of these resins may likewise be produced by conventional means, such as extrusion thru a slot die or by casting techiques.

Embossing is typically used on the surface of the polyolefin film to reduce gloss. For purposes of this invention a gloss of 8 or less is required for commercial acceptance of the film. Embossing can be imposed on the surface by an embossing roll at the time of the film fabrication or at a subseqent time by procedures well known in the art. The embossing roll should have an engraved surface that when measured with a Surtronic 3 apparatus (further identified in the Example) provides a maximum Ra reading of 45, preferably no greater Ra than 35, optimally Ra is no greater than 30.

The following examples are presented to illustrate the general concept disclosed herein and to demonstrate the advantage to be obtained by practice of this invention.

EXAMPLE

A film (A) was prepared in accordance with this invention by melt extruding polyethylene granules into a nominal 0.001 inch thick film and melt embossing it using an engraved roll with an average roughness (Ra) of 28 and average maximum profile height ($R_{pm}$) of 125 (both measured with a Surtronic 3 Apparatus sold by Taylor-Hobson, Guthlaxton Street, Leicester, England). The film was tested for gloss, tape adhesion and surface characteristics.

For comparative purposes, a second polyethylene embossed film (B) was similarly produced and tested except that a different engraved roll having an Ra of 63 and $R_{pm}$ of 225 was used.

The test results of both films A and B are shown in the following table.

TABLE 1

| | SAMPLE A | SAMPLE B |
|---|---|---|
| Gloss[1] | 4.2 | 3.5 |
| Tape Adhesion[2] | 330 | 200 |
| $R_{tm}$* | 163 | 300 |
| $R_{pm}$* | 66 | 166 |
| Ra* | 24–28 | 53–58 |

[1]Measurement of stack of film 10 layers thick with Gardner. Digital Photometric Unit PG-5500, Gardner Instruments, Bethesda, Md.
[2]Tested according to Proctor & Gamble Paper Products Co., Cincinnati, Ohio Analytical Method, page 3350-6, Backsheet Tape Adhesion Value, dated 5/30/80 where the higher number is better.
*Quantitative data from Surtronic 3.

The data of the table show that the tape adhesion is increased by 165 percent when the embossed film is produced according to this invention relatively to that prepared and marketed prior to this invention.

The invention in its broader aspect is not limited to the specific details shown and described and departures may be made from such details without departing from the principles of the invention and without sacrificing its chief advantages.

What is claimed is:

1. A disposable diaper having a diaper back sheet of polyolefin, non-woven top sheet, absorbent inner layer and tape closure tabs, wherein the exposed surface of said diaper back sheet has a 45° gloss of no greater than 8, a mean value of maximum profile height ($R_{pm}$) of less than 100 microinches and a mean maximum peak to valley height ($R_{tm}$) of less than 200 microinches, wherein said surface has enhanced adhesion to said tape closure tabs.

2. A disposable diaper according to claim 1 wherein said exposed surface has a $R_{pm}$ of less than 80 and a $R_{tm}$ of less than 160.

3. The disposable diaper according to claim 5 wherein the diaper back sheet is linear low density polyethylene, crystalline polypropylene or blends thereof.

* * * * *